US00PP14218P29

(12) United States Plant Patent
Lommerse

(10) Patent No.: US PP14,218 P2
(45) Date of Patent: Oct. 7, 2003

(54) DAHLIA PLANT NAMED 'KIEDAHBIC'

(50) Latin Name: *Dahlia variabilis*
Varietal Denomination: Kiedahbic

(75) Inventor: Henry Lommerse, Mariahout-Laarbeek (NL)

(73) Assignee: Kieft Seeds Holland, Venhuizen (NL)

( * ) Notice: Subject to any disclaimer, the term of this patent is extended or adjusted under 35 U.S.C. 154(b) by 0 days.

(21) Appl. No.: 10/163,016

(22) Filed: Jun. 5, 2002

(51) Int. Cl.[7] ..... A01H 5/00
(52) U.S. Cl. ..... Plt./321
(58) Field of Search ..... Plt./321

(56) References Cited

PUBLICATIONS

UPOV–ROM GTITM Plant Variety Database, 2003/01, GTI Jouve Retrieval Software, Citation for Dahlia 'Kiedahbic'.*

* cited by examiner

*Primary Examiner*—Bruce R. Campell
*Assistant Examiner*—June Hwu
(74) *Attorney, Agent, or Firm*—C. A. Whealy

(57) ABSTRACT

A distinct cultivar of Dahlia plant named 'Kiedahbic', characterized by its upright and compact plant habit; freely branching habit, full and dense plants; semi-double type inflorescences; and purple and white bi-colored ray florets with bright yellow-colored disc florets.

1 Drawing Sheet

Botanical classification/cultivar designation: *Dahlia variabilis* cultivar Kiedahbic.

BACKGROUND OF THE INVENTION

The present Invention relates to a new and distinct cultivar of Dahlia plant, botanically known as *Dahlia variabilis*, commercially referred to as a pot-type Dahlia, and hereinafter referred to by the cultivar name Kiedahbic.

The new Dahlia is a product of a planned breeding program conducted by the Inventor in Mariahout, The Netherlands. The objective of the breeding program is to create new pot-type Dahlia cultivars with desirable inflorescence form and attractive ray floret coloration.

The new Dahlia originated from a cross-pollination made by the Inventor in 1997 of a proprietary *Dahlia variabilis* selection identified as code number 96.1750, not patented, as the female, or seed, parent with a proprietary *Dahlia variabilis* selection identified as code number 97.1335, not patented, as the male, or pollen, parent. The new Dahlia was discovered and selected by the Inventor as a single flowering plant within the progeny of the stated cross-pollination grown in a controlled environment in Mariahout, The Netherlands.

Asexual reproduction of the new Dahlia by vegetative tip cuttings was first conducted in Mariahout, The Netherlands in 1997. Asexual reproduction by cuttings has shown that the unique features of this new Dahlia are stable and reproduced true to type in successive generations.

SUMMARY OF THE INVENTION

The cultivar Kiedahbic has not been observed under all possible environmental conditions. The phenotype may vary somewhat with variations in environment such as temperature and daylength, without, however, any variance in genotype.

The following traits have been repeatedly observed and are determined to be the unique characteristics of 'Kiedahbic'. These characteristics in combination distinguish 'Kiedahbic' as a new and distinct pot-type Dahlia:

1. Upright and compact plant habit.
2. Freely branching habit, full and dense plants.
3. Semi-double type inflorescences.
4. Purple and white bi-colored ray florets with bright yellow-colored disc florets.

Compared to plants of the female parent, the selection 96.1750, plants of the new Dahlia are larger and flower earlier. Compared to plants of the male parent, the selection 97.1335, plants of the new Dahlia have darker-colored ray florets and flower earlier.

Plants of the new Dahlia can be compared to plants of the Dahlia cultivar Select Pink, not patented. In side-by-side comparisons conducted in Venhuizen, The Netherlands, plants of the new Dahlia were more compact, flowered earlier, and differed in ray floret coloration.

BRIEF DESCRIPTION OF THE PHOTOGRAPHS

The accompanying colored photographs illustrate the overall appearance of the new Dahlia showing the colors as true as it is reasonably possible to obtain in colored reproductions of this type. Colors in the photographs may differ from the color values cited in the detailed botanical description which accurately describe the colors of the new Dahlia.

The photograph at the top of the sheet comprises a side perspective view of a typical flowering plant of 'Kiedahbic'.

The photograph at the bottom of the sheet is a close-up view of a typical inflorescence bud, upper surfaces of developing and fully opened inflorescences, lower surface of a typical inflorescence, and the upper and lower surfaces of typical leaves of 'Kiedahbic'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown and flowered during the winter and early spring in Lompoc, Calif., under commercial practice in a polycarbonate-covered greenhouse with day temperatures about 18 to 24° C., night temperatures about 16 to 18° C., and light levels about 4,000 to 8,000 foot-candles. Three cuttings were planted per 15-cm container and plants were grown for about 10 weeks.

Botanical classification: *Dahlia variabilis* cultivar Kiedahbic.

Parentage:

*Female, or seed, parent.*—Proprietary *Dahlia variabilis* selection identified as code number 96.1750, not patented.

*Male, or pollen, parent.*—Proprietary *Dahlia variabilis* selection identified as code number 97.1335, not patented.

Propagation:

*Type.*—Terminal tip cuttings.

*Time to rooting.*—Summer: About 8 days at 22° C. Winter: About 10 days at 22° C.

*Time to develop a rooted cutting.*—Summer: About 16 days at 20° C. Winter: About 20 days at 20° C.

*Root description.*—Fine to somewhat thick, fleshy; development of tubers has not been observed.

Plant description:

*Appearance.*—Herbaceous pot-type Dahlia. Inverted triangle; stems mostly upright and somewhat outwardly spreading giving a uniformly mounded appearance to the plant; relatively compact. Freely branching, about five to seven lateral branches per plant; dense and full plants.

*Plant height.*—About 16 cm.

*Plant width or area of spread, single plant.*—About 15.5 cm.

*Lateral branches.*—Length: About 12 cm. Diameter: About 3 mm. Internode length: About 2.5 cm. Strength: Strong. Texture: Smooth, glabrous. Color: 144D.

*Foliage description.*—Arrangement: Leaves simple; opposite. Length: About 5 cm. Width: About 2.2 cm. Shape: Elliptical, elongated. Apex: Acute. Base: Attenuate. Margin: Serrate. Texture, upper and lower surfaces: Smooth, glabrous. Petiole length: About 1.5 cm. Petiole diameter: About 3 mm. Petiole texture, upper and lower surfaces: Smooth, glabrous. Color: Young foliage, upper surface: 146A. Young foliage, lower surface: 147B. Mature foliage, upper surface: 146A. Mature foliage, lower surface: 147B. Venation, upper surface: 147C. Venation, lower surface: 147B. Petiole, upper and lower surfaces: 144C.

Inflorescence description:

*Appearance.*—Terminal and axillary semi-double type inflorescences held above and beyond the foliage on strong flexible peduncles; inflorescences face upright. Composite inflorescence form with elongated oblong to elliptical-shaped ray florets and disc florets massed at the center; ray and disc florets arranged acropetally on a capitulum. Inflorescences not fragrant. Inflorescences persistent. Flowering response: Plants flower continuous and freely from April until October in Northern Europe.

*Postproduction longevity.*—Inflorescences maintain good color and substance for about four to five days on the plant.

*Quantity of inflorescences.*—During the flowering season, about 100 inflorescences per plant may develop.

*Inflorescence bud* (*stage of showing color*).—Shape: Oblate. Length: About 1.2 cm. Diameter: About 1 cm. Color: 82B to 82C.

*Inflorescence size.*—Diameter: About 3.5 cm. Depth (height): About 1.5 cm. Diameter of disc: About 7 to 12 mm.

*Ray florets.*—Shape: Elongated-oblong to elliptical. Aspect: Straight, slightly concave. Length: About 1.8 cm. Width: About 8 mm. Apex: Broadly acute. Base: Attenuate. Margin: Entire. Texture: Smooth, glabrous, satiny. Number of ray florets per inflorescence: About 38 in about four rows. Color: When opening, upper surface: 82A. When opening, lower surface: 82B to 82C. Fully opened, upper surface: Towards apex, 82B; towards mid-section, 82C; towards base, 155A; base, 10D; color does not fade with subsequent development. Fully opened, lower surface: Towards apex, 82B; mid-section, 82D; towards base and longitudinal stripes, 155A.

*Disc florets.*—Shape: Tubular, elongated. Apex: Five-pointed. Length: About 1 cm. Width: Apex, about 2 mm; base, about 1 mm. Number of disc florets per inflorescence: About 56. Color: Immature: 12A. Mature: Apex: 12A. Mid-section: 2B. Base: 157B.

*Involucral bracts.*—Quantity: About 40 yellow-green bracts subtended by 5 darker green bracts, imbricate. Yellow-green length: About 1.1 cm. Width: About 5 mm. Darker green length: About 8 mm. Width: About 3 mm. Shape: Elliptical. Apex: Acute. Base: Truncate. Margin: Entire. Texture: Smooth, thin. Color, upper and lower surfaces: Yellow-green, 150C; darker green, 138A.

*Peduncles.*—Length: About 3.5 cm. Diameter: About 1.5 mm. Strength: Strong, very flexible. Aspect: Upright. Texture: Smooth, glabrous. Color: 144A.

*Reproductive organs.*—Androecium: Present on disc florets only. Anther color: 14A. Pollen amount: Scarce to none. Pollen color: 14A. Gynoecium: Present on both ray and disc florets. Stigma color: 12A. Style color: 2B.

*Seed/fruit.*—Seed and fruit production has not been observed.

Disease/pest tolerance: Plants of the new Dahlia have not been observed to be tolerant to pathogens and pests common to Dahlias.

Weather tolerance: Plants of the new Dahlia have been observed to be wind and rain-tolerant; and have been observed to be tolerant to temperatures ranging from 12 to 30° C.

It is claimed:

1. A new and distinct cultivar of Dahlia plant named 'Kiedahbic', as illustrated and described.

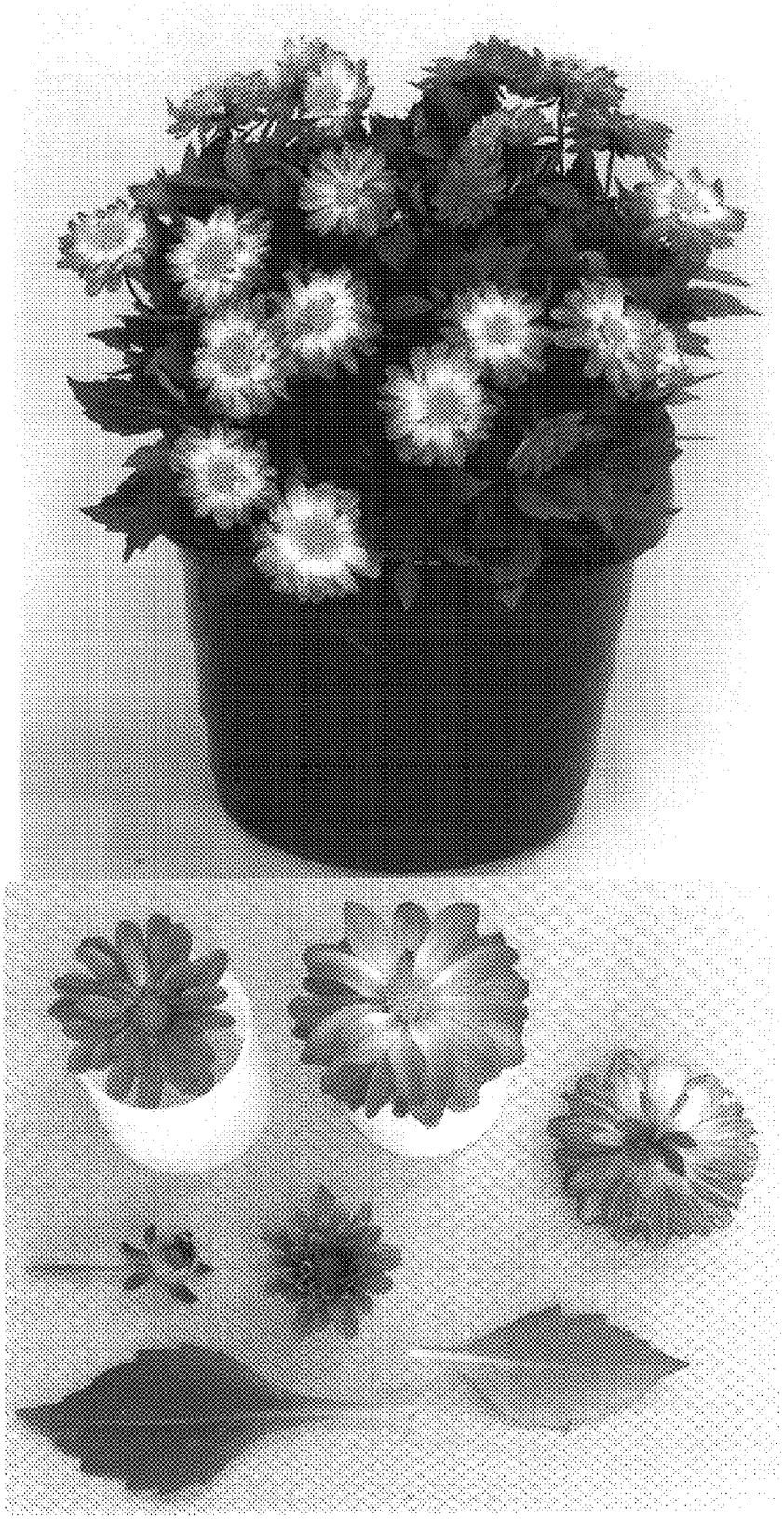

* * * * *